United States Patent [19]

Kakkar et al.

[11] Patent Number: 5,576,304
[45] Date of Patent: Nov. 19, 1996

[54] ANTITHROMBOTIC COMPOSITION

[75] Inventors: Vijay V. Kakkar, Bickley; Michael F. Scully, Crays Hill, both of Great Britain

[73] Assignee: Thrombosis Research Institute, London, Great Britain

[21] Appl. No.: 688,931

[22] PCT Filed: Nov. 9, 1989

[86] PCT No.: PCT/EP89/01341

§ 371 Date: Jul. 9, 1991

§ 102(e) Date: Jul. 9, 1991

[87] PCT Pub. No.: WO90/04970

PCT Pub. Date: May 17, 1990

[30] Foreign Application Priority Data

Nov. 11, 1988 [GB] United Kingdom ............ 8826448

[51] Int. Cl.$^6$ .................... A61K 31/725; C08B 37/10
[52] U.S. Cl. .................. 514/56; 514/54; 536/21; 536/54; 536/112; 536/118
[58] Field of Search ............. 514/54, 56; 536/21, 536/54, 112, 118

[56] References Cited

U.S. PATENT DOCUMENTS

| | | | |
|---|---|---|---|
| 4,687,765 | 8/1987 | Vairel et al. | 514/56 |
| 4,804,652 | 2/1989 | Lormeau et al. | 514/56 |
| 4,908,354 | 3/1990 | Seidel et al. | 514/56 |
| 4,973,580 | 11/1990 | Mascellani et al. | 514/54 |
| 5,008,253 | 4/1991 | Casu et al. | 514/54 |
| 5,164,377 | 11/1992 | Van Dedem et al. | 514/54 |

FOREIGN PATENT DOCUMENTS

| | | |
|---|---|---|
| 2622450 | 3/1987 | France . |
| 997727 | 7/1965 | United Kingdom . |

OTHER PUBLICATIONS

Yin, E. T. et al., J. Lab. Clin. Med. (1973) 81:298–310.
Anderson, L.-O. et al. Thrombosis Research (1976) 9:575.
Pulver, V. R. Arzneimittel–Forschung (1965) 15:11.
Copley et al; Biorheology 20:697–704 (1983).
Cade et al; Thrombosis Research 35:613–625 (1984).
Bianchini et al; Thrombosis Research 40:597–607 (1985).
Cella et al; Chemical Abstracts 106:211619d (1987).
Hatanaka et al; J. Med. Chem. 30:810–814 (1987).
Stassen et al; Chemical Abstracts 108:68585y (1988).
Scully et al; Chemical Abstracts 109:145162h (1988).
Ofosu et al; Chemical Abstracts 110:50984j; 50985k (1989).

*Primary Examiner*—Gary L. Kunz
*Assistant Examiner*—Kathleen Kahler Fonda
*Attorney, Agent, or Firm*—Walter H. Dreger

[57] ABSTRACT

A pharmaceutical composition comprising dermatan sulphate, together with a low molecular weight heparin, free or fixed combination, is useful as a antithrombolytic agent with a low risk of bleeding complications.

10 Claims, No Drawings

ANTITHROMBOTIC COMPOSITION

This invention relates to pharmaceutical compositions for the prevention of thrombotic conditions, particularly for the prophylaxis of deep vein thrombosis following major surgery.

Heparin has been used for many years as an agent for the treatment and the prevention of thrombosis. The mechanism of the anticoagulant activity of heparin is now essentially known. The coagulation of blood is a cascade-like process in which a number of proteolytic enzymes activate each other in a definite sequence. In the last stage fibrinogen is converted under the action of the proteolytic enzyme thrombin to insoluble fibrin which is the fundamental structure in a blood clot. The coagulation process is further regulated through the inhibiting activity of at least two plasma proteins i.e., antithrombin III (AT III) and heparin cofactor II (HC II). AT III and HC II are homologous proteins which differ in the range of proteases that each inhibits. HC II inhibits thrombin but not factor Xa while AT III inhibits both of these as well as several other proteases involved in coagulation and fibrinolysis.

When added to blood or plasma, heparin acts on various steps of the coagulation process. In particular, by forming complexes with AT III and HC II, it increases their inhibitory effect on most of the inhibition-sensitive enzymes. Thus, as heparin is able to simultaneously depress a large number of the clotting factors, its anti-clotting activity does not appear specific but general.

However, an essential aspect of the activity of heparin consists in the inhibition of factor Xa through activation of AT III. In the middle of the coagulation cascade, factor Xa has a central and important position since it is directly involved in the transformation of pro-thrombin into thrombin. The inhibition of thrombin formation is considered especially important to obtain an effective thrombosis-preventing effect.

It is known that whole heparin is an heterologous polysaccharide with respect both to the composition and the length of its oligosaccharide chain. Whole heparin is a mixture of components of molecular weight from 2 to 40 kD, having an average molecular weight of about 15 kD. Whole heparin may be fractionated by molecular weight, each fraction retaining a heparin-like activity.

The activity of heparin (whole heparin or heparin fragments) as an anti-thrombotic agent may be measured as its specific anti factor Xa activity in the Yin-Wessler test described in J. Lab. Clin. Med. (1973) 81: 298–310. As is well known, the Yin-Wessler activity is representative of the capacity of heparin to potentiate the inhibition of factor Xa by AT III. The specific activity of whole standard heparin for factor Xa is about 150 I.U./mg as defined according to the third International Heparin Standard.

The global anti-clotting activity, i.e. the capacity to prolong the clotting time of blood or plasma may be conveniently measured according to the activated partial thromboplastin time (APTT) method as described in Thrombosis Research (1976) 9: 575. The specific activity of whole standard heparin in the APTT test is fixed by definition so that the ratio between antifactor Xa and APTT specific activities is equal to 1:1, that is, it is also about 150 I.U./mg.

Although whole heparin turns out to be a valuable drug, its use is associated with the risk of haemorrhagic complications if too high a dose is given. Bleeding complications, which are believed to be related to the global anti-clotting action of heparin, especially to the interference with platelet/collagen interaction, are observed at concentration of heparin at which APTT is excessively prolonged. A crucial aspect of the problem is that the dosage must be balanced in such a manner that a good thrombosis protection is obtained simultaneously as bleeding complications are avoided. In general practice, the heparin dosage should be controlled such that the APTT clotting time does not exceed three times the initial clotting time measured in the absence of any anticoagulant agent. However, such a dosage is a delicate operation because of the great individual variation between different patients.

More recently it has been shown that the lower molecular weight (LMW) fractions of heparin have a more selective action than whole heparin. By the term "a low molecular weight heparin" is meant a heparin prepared, e.g. by fractionation or by depolymerisation as hereinafter described, so as to achieve significant reduction of average molecular weight as compared with whole heparin preparations. LMW heparin is capable of enhancing the activity of AT III with respect to a smaller number of clotting factors as well as of regulating the inhibition of these factors with a different degree of effectiveness.

More particularly, LMW heparins have a specific anti-factor Xa activity similar to that of heparin while their activity on global coagulation is significantly lower e.g. about 50 I.U./mg as measured in the APTT test. Accordingly, their anti-factor Xa/APTT ratio is approximately 3–5 (so that they activate the interaction of AT III with factor Xa about 3–5 times more readily than that of AT III and HC II with thrombin).

The practical effect of this is that low molecular weight heparin is as effective an antithrombotic agent as normal heparin, but is less likely to give rise to bleeding complications.

A number of sulphated polysaccharides have been identified as having the property of prolonging the clotting time of blood or plasma and these have been grouped under the heading of heparinoids. They tend to be similar to LMW heparins with an anti-factor Xa/APTT ratio of 1.5–3 but are about 10 times less potent than heparin. Their heparin-like activity is believed to be essentially due to activation of the thrombin inhibitor HC II. Though heparinoids have a weaker antifactor Xa activity they have been used in replacement of heparin in antithrombotic treatments because they can be administered to achieve very high concentrations in blood without having an effect on platelets or bleeding side effects. Examples of heparinoids include heparan sulphate, dermatan sulphate (also called chondroitin sulphate B), pentosan polysulphate, dextran sulphate and chondroitin sulphates K and H.

The activities of LMW heparins and heparinoids were originally expected to be at best strictly additive. However, it has now surprisingly been found that the antifactor Xa activity of a LMW heparin is enhanced in a synergistic manner by addition of a heparinoid, while only an additive effect is to be found for the APTT activity which remains low. In consequence both the overall antithrombotic activity and the anti-factor Xa/APTT ratio are improved so that the combination is more effective in the prophylaxis of thrombosis than either component alone, and less likely to give bleeding complications at an effective antithrombotic dose than LMW heparin alone.

Accordingly, the present invention provides a method for the prophylaxis of deep vein thrombosis in a patient in need of such treatment comprising the administration of jointly effective amounts of a LMW heparin and a heparinoid, either simultaneously or sequentially within a time interval close enough to provide a synergistic effect. It will be appreciated by those skilled in the art that a sequential administration may be either carried out by first administering a LMW and then a heparinoid or carried out in reverse order.

Alternatively, the invention also provides the use of a heparinoid together with a LMW heparin, in free or fixed combination, as an anti-thrombotic agent. As a further alternative, there is also provided the use of a heparinoid for potentiation of the anti-thrombotic effect of LMW heparin.

By "synergistic effect" is meant an anti factor Xa activity greater than would be expected from the additive effect of the heparinoid and the LMW heparin when administered independently.

For use in the present invention, the preferred heparinoid is dermatan sulphate which is a mucopolysaccharide consisting of a repetition of disaccharide units of iduronic acid and galactosamine-4-sulphate. Dermatan sulphate as other glycosaminoglycans is widely distributed in fibrous connective tissues, including tendon, skin, sclera, Joint capsule, aorta and fibrous cartilage. It may be prepared in substantially pure form according to methods known in the art e.g. those described in EP 97 625 and EP 238 994. Dermatan sulphate is also commercially available from porcine intestinal mucosa.

LMW heparins for use in the present invention preferably have an average molecular weight of 10 kD or less, more preferably of 8 kD or less, most preferably less than 5 kD. It is further preferred that LMW heparins should be of relatively uniform molecular weight e.g. with at least 60%, more preferably 80% of polymer units having a molecular weight within the above defined average molecular weight limits.

Suitable pharmaceutically acceptable salts of LMW heparins are e.g. the calcium and potassium and, in particular, the sodium salt.

LMW heparins or pharmaceutically acceptable salts therefore may be obtained in accordance with methods known in the art, e.g. by isolation of low molecular weight fractions from whole heparin preparations, e.g. by fractional precipitation and filtration, for example as described in German Offenlegungsschrift No. 29 45 591, or by depolymerisation of high molecular weight fractions of whole heparin e.g. by chemical cleavage, for example as described in Belgian Patent No. 888,864 or European Patent Publication No. 27,089. Alternatively LMW heparins may be obtained by a combination of such techniques, e.g. by separation of LMW heparin from whole heparin preparations, followed by depolymerisation of remaining higher molecular weight heparin fractions to yield further low molecular weight heparin and, optionally, combination of the two LMW heparin preparations thus obtained.

Where LMW heparin is prepared by chemical cleavage, individual chain residues may undergo a measure of chemical modification in particular de-sulphatisation. Where this occurs, LMW heparin for use in accordance with the present invention may, if desired, subsequently be reconstituted or otherwise appropriately modified in accordance with known techniques, for example analoguously to the techniques disclosed in Belgian patent specification No. 888,864.

Where LMW heparin preparations obtained by chemical cleavage are used in the compositions of the invention, these will preferably be preparations which have undergone no, or substantially no additional chemical modification.

For administration in patients, a heparinoid and a LMW heparin, separately or together, are admixed with a pharmaceutically acceptable liquid carrier, e.g. sterile water or sterile isotonic saline and are preferably injected or infused by the intravenous route.

The preferred ratio of the components administered in combination lies between 1:1 and 1:10 LMW heparin:heparinoid by weight, more preferably between 1:3 and 1:10.

Preferably the patient receives simultaneously a) a unit dose containing an amount of heparinoid for which an approximately twofold increase of the clotting time over control (plasma without any addition of heparinoid) is observed when heparinoid alone is assayed in an APTT test and b) a unit dose containing an amount of LMW heparin sufficient to confer to the plasma of the patient an anti-factor Xa activity of from 0.05 to 0.6 international heparin unit/ml. This treatment may be repeated at regular intervals as long as it is required.

For ease of administration, it may be preferred to administer a mixture of a heparinoid and of LMW heparin in a single injection. According to a further aspect of the invention, there is provided a pharmaceutical composition comprising either a mixture of a heparinoid and an LMW heparin together with a pharmaceutically acceptable diluent or carrier e.g. sterile water for injection or sterile isotonic saline or a mixture of a heparinoid and a LMW heparin in lyophilised or freeze dried solid form to which sterile water or saline is added before injection. Preferably the composition is made up in unit dosage forms e.g. vials for injection, each containing a) an amount of heparinoid for which an approximately twofold increase of the clotting time over control is observed when heparinoid alone is assayed in an APTT test and b) an amount of LMW heparin sufficient to confer to the unit dosage form an anti-factor Xa activity of from 0.05 to 0.6 international unit/ml.

The component of the synergistic mixture of the invention may also be presented in twin-pack form, that is, as a single package containing separate unit dosages of a heparinoid and an LMW heparin with instructions for concomitant administration. The unit dosage forms for injection may be sterile solutions of a heparinoid or a LMW heparin in pure water or in physiological saline or may be in lyophilised or freeze dried solid form to which sterile water or saline is added before injection. The quantity of heparinoid and LMW heparin in the unit dosage form for injection are those as above described.

The solutions for injection, i.e. the compositions or the separate unit doses may contain other components for example buffer salts such as $Na_2HPO_4/NaH_2PO_4$ and preservatives e.g. mannitol and human albumin. These components may also be present in the lyophilised or freeze dried forms.

The quantity of each compound is expressed herein either by weight (mg) or in International Units (I.U.) based on the third International Standard heparin assayed according to Hardisty R.M. and Ingram G.I.C. (1965), Bleeding Disorders; Blackwell Scientific Publications, Oxford.

EXAMPLE 1

A solution of heparin 4 (molecular weight=4 kD) was prepared in plasma at a concentration at which a doubling of the clotting time over control (plasma alone) is observed in an anti-factor Xa test (Heptest). 25 µg/ml dermatan sulphate (anti-Xa/APTT ratio=1–1.5) were added to an aliquot of the preparation. This aliquot was tested for its antithrombotic and anti-clotting activities together with an aliquot of plasma solution containing heparin 4 alone.

The APTT activity was measured as described in Andersson et al, Thrombosis Research 9: 575–83 (1976). 0.1 ml of a heparin dilution was added to 0.1 ml plasma, followed by 0.1 ml of a suspension of kaolin (5 mg/ml, B.D.H.) in saline at 37° C. After 9.75 min 0.1 ml Bell and Alton reagent was added, and at 10 min 0.1 ml 0.025M $CaCl_2$. Clotting times were then measured using an automated coagulometer. The clotting time observed in the presence of dermatan sulphate was similar to that measured in the absence of dermatan sulphate. This in particular suggests that Dermatan sulphate has no significant effect on the anti-clotting activity of heparin.

The antifactor Xa activity was measured according to the Yin and Wessler method using a commercial kit (Heptest<sup>R</sup> Haemachem Inc. St. Louis, Mo. 63144, USA). To 0.1 ml of plasma aliquots prepared as above was added 0.1 ml of factor Xa at 37° C. After 120 s., clotting was initiated by addition of 0.1 ml of a $CaCl_2$/phospholipid mixture (Recalmix<sup>R</sup>). Clotting times were then recorded and converted to unit heparin/ml using a standard calibration curve as reported in Table 1.

Since the addition of dermatan sulphate results in a 16-fold increase of the anti-factor Xa activity it may be concluded that a synergistic interaction between dermatan sulphate and heparin 4 is to be found within the antifactor Xa (antithrombotic) activity whereas the clotting activity is not significantly modified. Thus, the anti-factor Xa/APTT ratio of the combination may be calculated as a 16-fold increase of the ratio corresponding to heparin 4 alone. This significant increase reveals that the combination is better for anti-thrombotic use than dermatan sulphate or heparin 4 alone in that it is less likely to give bleeding side effects.

EXAMPLE 2

Example 1 is repeated with solutions of LHW heparins of a molecular weight of 2, 6, 8 and 15 kD. In the APTT test, the clotting times of each LMW heparin and the combination thereof with dermatan sulphate were found similar. The anti-factor Xa/APTT ratio of each combination was calculated as described in Example 1. With regard to heparins 2, 6, 8 and 15, the ratios of the combinations are 42:1, 11.6:1, 8.5:1 and 4:1 respectively.

EXAMPLE 3

350 mg of dermatan sulphate and 200 I.U. of a LMW heparin with an average molecular weight of 4 kD are dissolved in 2 ml sterile isotonic vial saline and packaged in a vial for injection.

Such a composition can achieve similar therapeutic effects than those observed when 5000 I.U; of LMW heparin is given.

EXAMPLE 4

After surgery a male patient received over a 10-day period a daily injection of 1 ml of a mixture of heparin 4 and dermatan sulphate which anti-factor Xa activity was 5000 I.U./ml as measured in a Heptest with the plasma patient. No bleeding complication was observed.

TABLE 1

| LMW heparin | heparin 4 (4 kD) |
| --- | --- |
| Anti factor Xa/AAPTT ratio of LHW heparin | 3:1 |
| Anti factor Xa activity of LMW heparin alone | 0.05 I.U../ml |
| Anti factor Xa activity of LMV heparin in the presence of 25 µg/ml Dermatan sulphate | 0.8 I.U./ml |
| Anti factor Xa/APTT ratio of LHW heparin in the presence of 25 µg/ml Dermatan sulphate | 48:1 |

We claim:
1. A method for increasing the anti-factor Xa activity within the bloodstream of a patient in need thereof, comprising simultaneously co-administering a mixture of dermatan sulphate and a low molecular weight heparin, wherein said mixture exhibits a synergistic enhancement of the anti-factor Xa activity with only an additive enhancement of the APTT activity, such that the anti-factor Xa/APTT activity ratio of the mixture is increased as compared with either component tested alone.

2. The method according to claim 1 in which the low molecular weight heparin has an average molecular weight of less than 5 kD.

3. A pharmaceutical composition comprising either (a) a mixture of a low molecular weight heparin and dermatan sulphate together with a pharmaceutically acceptable diluent or carrier or (b) a mixture of a low molecular weight heparin and dermatan sulphate in lyophilized or freeze-dried form, wherein said mixture exhibits a synergistic enhancement of the anti-factor Xa activity with only an additive enhancement of the APTT activity, such that the anti-factor Xa/APTT activity ratio of the mixture is increased as compared with either component tested alone.

4. A composition according to claim 3 in which the weight ratio of the low molecular weight heparin to dermatan sulphate is from 1:1 to 1:10.

5. A composition according to claim 4 in which the weight ratio of the low molecular weight heparin to dermatan sulphate is from 1:3 to 1:10.

6. A composition according to claim 3 in which the low molecular weight heparin has an average molecular weight less than 5 kD.

7. A composition of unit dosage for administration to a patient according to claim 3 comprising an amount of a mixture of dermatan sulphate and a low molecular weight heparin, wherein said amount is sufficient to confer to said patient an antifactor Xa activity of from about 0.05 to 0.6 international heparin units/ml, wherein said mixture exhibits a synergistic enhancement of the anti-factor Xa activity with only an additive enhancement of the APTT activity, such that the anti-factor Xa/APTT activity ratio of the mixture is increased as compared with either component tested alone.

8. A kit comprising: a) a unit dosage of dermatan sulphate; b) a unit dosage of a low molecular weight heparin; and c) instructions for the co-administration of said dosage of dermatan sulphate and said dosages of low molecular weight heparin, wherein the mixture of said dermatan sulphate and said low molecular weight heparin exhibits a synergistic enhancement of the anti-factor Xa activity with only an additive enhancement of the APTT activity, such that the anti-factor Xa/APTT activity ratio of the mixture is increased as compared with either component tested alone.

9. A kit according to claim 8 in which the low molecular weight heparin has an average molecular weight less than 5 kD.

10. The method of claim 1 wherein said simultaneous co-administration is effected by administering said dermatan sulphate and said low molecular weight heparin sequentially in any order.

* * * * *